United States Patent [19]

Pfirrmann

[11] Patent Number: 5,210,083

[45] Date of Patent: May 11, 1993

[54] PHARMACEUTICAL COMPOSITIONS

[75] Inventor: Rolf W. Pfirrmann, Lucerne, Switzerland

[73] Assignee: Ed. Geistlich Sohne A.G. fur Chemische Industrie, Lucerne, Switzerland

[21] Appl. No.: 672,010

[22] Filed: Mar. 19, 1991

Related U.S. Application Data

[63] Continuation of Ser. No. 552,359, Jul. 12, 1990, abandoned, which is a continuation of Ser. No. 408,425, Sep. 14, 1989, abandoned, which is a continuation of Ser. No. 298,857, Jan. 19, 1989, abandoned, which is a continuation of Ser. No. 74,875, Jul. 17, 1987, abandoned.

[30] Foreign Application Priority Data

Jul. 17, 1986 [GB] United Kingdom ............ 8617482

[51] Int. Cl.$^5$ .............................. A61K 31/54

[52] U.S. Cl. .................................. 514/222.5

[58] Field of Search ...................... 514/222.5

[56] References Cited

U.S. PATENT DOCUMENTS 4,587,268 5/1986 Pfirrmann ........................ 514/222
4,626,536 12/1986 Pfirrmann ........................ 514/222

FOREIGN PATENT DOCUMENTS 0162705 5/1985 European Pat. Off. .
7612644 11/1976 France .

Primary Examiner—Jerome D. Goldberg
Attorney, Agent, or Firm—Rothwell, Figg, Ernst & Kurz

[57] ABSTRACT

An aqueous solution containing a bacterially effective concentration of taurolidine and/or taurultam together with a parenterally acceptable polyol. The aqueous solution is particularly suitable for parenteral administration.

10 Claims, No Drawings

PHARMACEUTICAL COMPOSITIONS

This is a continuation of application Ser. No. 07/552,359, filed Jul. 12, 1990, which is a continuation of application Ser. No. 07/408,425 filed on Sep. 14, 1989, which is a continuation of application Ser. No. 07/298,857 filed on Jan. 19, 1989, which is a continuation of application Ser. No. 07/074,875 filed Jul. 17, 1987 all abandoned.

This invention relates to formulations of taurolidine and/or taurultam, primarily for parenteral administration.

The antibacterial compounds taurolidine and taurultam have the following formulae:

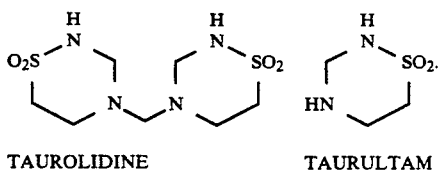

TAUROLIDINE             TAURULTAM

These compounds are condensation products of formaldehyde with taurinamide and are active not only against both gram-positive and gram-negative bacteria but also against exotoxins and endotoxins produced by these organisms.

The mode of action of taurolidine has been shown to include the transfer of methylol groups to hydroxyl or amino groups present on the above toxins or on the mureine of the bacterial cell walls. In solution, taurolidine exists in equilibrium with taurultam and N-methylol taurultam, taurolidine being greatly predominant. Taurultam is itself in equilibrium with methylol taurinamide, the equilibrium being greatly in favour of taurultam. When the above methylol derivatives, methylol taurultam and methylol taurinamide, contact the toxins or bacteria, methylol groups are transferred. Methylol taurultam is thereby converted to taurultam, while methylol taurinamide is converted to taurine, a naturally occurring aminosulphonic acid which is extremely well tolerated in the human body. It will thus be appreciated that taurolidine and taurultam act in essentially the same way and produce the same final products.

Taurolidine and taurultam have previously been proposed primarily for use in maintaining sterility in surgical operations where gross infection with bacteria and bacterial toxins was likely, for example in cases of peritonitis. More recently, however, it has been found that bacterial toxaemia can advantageously be treated parenterally. Bacterial endotoxins and exotoxins are primarily responsible for many of the most serious pathological effects of bacterial infections. When such toxins are present at above certain concentrations, the patient can suffer septic shock. It is often found that use of antibiotics is contra-indicated in the case of some gram-negative bacterial infections due to the release of large quantities of endotoxins when the cell walls of gram-negative bacteria are attacked by the antibiotic. It is thus particularly useful in such cases to be able to administer taurolidine and taurultam parenterally, for example intravenously both to combat infections and to deal with septic shock.

However, the water-solubility of both compounds is relatively low, namely 1 g/liter in the case of taurolidine and 8 g/liter in the case of taurultam. Relatively large quantities of the compounds are required where toxaemia is well established and even where the compounds are administered in large volumes by intravenous infusion, low solubility can limit their use. In particular, during treatment of patients suffering from septic shock and consequent renal insufficiency, administration of significant quantities of liquid (after an initial period of volume compensation) is contra-indicated and the intravenous infusion solution should be as concentrated as possible. Where glucose is present, this is also beneficial in such cases in order to support the brain cells.

Taurolidine has previously been formulated in aqueous solution at concentrations up to 2% by weight by incorporating polyvinyl pyrrolidone as a crystallisation inhibitor. At higher concentrations of taurolidine, however, crystallisation can occur, so rendering the solutions unuseable.

In view of the mode of action of taurolidine mentioned above, it was not initially thought suitable to use compounds containing hydroxyl groups to increase the solubility or inhibit the crystallisation of the compound. In the case of bacteria and their endo- and exotoxins, it has been found that after the methylol transfer as set out above, there is a further irreversible step involving dehydration. Thus, in the case of bacterial endotoxins, which are lypopolysaccharides, it is found that an irreversible cross-linking reaction takes place which prevents the endotoxin from exerting its lethal effect. Similarly, in the case of bacterial exotoxins, which are proteins or polypeptides and do not contain lypopolysaccharide material of the kind found in the endotoxins, the detoxification reaction is found to be irreversible. However, our investigations have shown that the transfer of methylol groups by the mechanism set out above is reversible in the case of many hydroxyl or amino compounds, so that an equilibrium is established which does not significantly interfere with the availability of taurolidine.

We have now found that surprisingly polyols such as sugars and sugar alcohols can be used to maintain relatively high concentrations of taurolidine and/or taurultam in aqueous solution without significantly effecting the antibacterial and antitoxin activity.

When 2% aqueous taurolidine (containing polyvinylpyrrolidone to aid solubility) is administered intravenously it has sometimes been observed that at high rates of infusion, short duration vagotonic side effects occur, such as meiosis, lachrymation, salivation, bradycardia and excitation. We have found that when taurolidine is administered in glucose solution rather than polyvinylpyrrolidone, such vagotonic effects are not observed. This is a surprising effect of considerable value in ensuring that taurolidine can be given intravenously at a rapid rate of infusion, for example in cases of endotoxin shock. In general, the overall intravenous tolerance of taurolidine is increased by the presence of glucose. The same advantages apply also to taurultam.

Furthermore, the beneficial effect observed with glucose can also be obtained using similar polyhydroxylic compounds such as glycerol, other sugars and also sugar alcohols.

Glycerol, sugars and sugar alcohols are commonly administered parenterally, e.g. intravenously, as components of nutritional solutions, which may additionally contain amino acids and trace elements. However, such solutions are often pyrogenic due to bacterial infection during formulation, which is extremely difficult to avoid. The pyrogens are not, of course, removed when the solutions are finally sterilised. We have found that taurolidine and taurultam are capable of detoxifying such pyrogens. Furthermore, although such nutritional solutions are sterile when infusion is started, there is inevitably transmission of infection from the patient to the solution via the intubation. We have found that incorporation of taurolidine and/or taurultam into such nutritional solutions at anti-bacterial concentrations has the added benefit of maintaining sterility during infusion.

Polyhydroxy compounds are difficult to sterilise by autoclaving due to side reactions which may occur. By including taurolidine or taurultam in bacterial quantities we have found it possible to sterilise the solutions by filtration procedures only.

Further, where amino acids are included in such nutritional solutions, the Maillard reaction can take place,. We have found that the presence of taurolidine or taurultam prevents or inhibits this reaction.

According to the present invention, therefore, we provide aqueous solutions containing a bacterially effective concentration of taurolidine and/or taurultam together with a parenterally acceptable polyol, such as a glycerol or sugar or sugar alcohol.

Suitable polyols for inclusion in the solutions of the invention include carbohydrates, e.g. hexoses such as glucose and fructose, (or mixtures of these such as invert sugar), pentoses such as xylose or polysaccharides such as dextran or hydrolysed starch; glycerol and sugar alcohols such as sorbitol, mannitol or xylitol.

Where the solutions are for use in intravenous infusion, to combat bacterial infections and/or toxic shock it is particularly useful if the polyol can be metabolised. For this reason, glucose and fructose are particularly useful and also sorbitol and xylitol. Glucose is advantageous in that it is particularly readily metabolised and, indeed, can provide a valuable nutritional element. On the other hand, fructose may be advantageous where a patient cannot tolerate large quantities of glucose, for example in cases of diabetes.

The concentration of taurolidine in the solution is preferably in the range 1 to 5%, advantageously 2 to 3%, by weight. The concentration of taurultam is preferably in the range 1 to 7.5%, advantageously 3 to 5%, by weight.

The concentration of the polyol can usefully be in the range 3-40% by weight, In the case of glucose, the concentration is preferably in the range 10-30% by weight, preferably 20%.

Thus, particularly preferred formulations according to the invention are aqueous solutions of taurolidine at a concentration in the range 2-4% by weight containing glucose at a concentration of 10-40% by weight. Formulations containing 3-4% by weight of taurolidine and 15-25% by weight of glucose are especially preferred.

Although the solutions according to the invention are surprisingly stable at room temperature, there is some evidence that reaction can occur at elevated temperatures, for example those used in sterilisation by autoclaving. Consequently, as indicated above, it is preferred that the formulations are prepared by dissolving the taurolidine or taurultam in an aqueous solution of the polyol, which may optionally previously be sterilised, for example by autoclaving, and to complete sterilisation by filtration. If autoclaving is used to sterilise solutions containg a polyol (and optionally taurolidine or taurultam) it is preferable that this be done rapidly, in the substantial absence of oxygen. Thus, the vessel containing the solution can be evacuated and the space above the liquid purged with an inert gas such as nitrogen prior to sealing, so as to provide a very low partial pressure of oxygen. Furthermore, the presence of heavy metals should be avoided.

Although polyols and, indeed amino acid solutions, are most stable at slightly acid pH, it is preferred that the solutions for infusion should be at about neutral pH.

The principal adverse reaction is the conversion of sugars such as glucose or fructose to aldehydes such as hydroxymethylfurfural and ultimately to acids. This reaction has been shown to be catalysed by aspartic acid, which will sometimes be a component of nutritional solutions containing amino acids. However, if the above precautions are taken, there is no difficulty in preparing the solutions of the invention in sterile form at an acceptable level of titratable acidity (e.g. 0.1 to 0.5,. equiv./liter). As indicated above, it is also possible to sterilise the solutions by filtration.

The solution will normally be at physiological pH. If necessary, the pH can be adjusted by the addition of an acid or a base. While mineral acids such as hydochloric acid can be used, it is preferred to use a metabolisable acid such as acetic, malic or lactic acid, which does not tend to cause acidosis. The pH can also be adjusted by electrolysis. The relatively high concentrations of sugar or sugar alcohol render the solutions hypertonic but this is physiologically acceptable and, indeed, not uncommon where glucose is used in intravenous alimentation.

Where taurolidine is administered by intravenous infusion in order to treat septic shock, a suitable dose will be 20–30 g taurolidine over a 24 hour period in the case of a 70 kg adult human patient. This will be administered conventionally by catheter. Where the solutions are intended for administration of taurolidine or taurultam as such, the polyol will conveniently be glucose and in general, no other components will be present.

Where the solutions are intended for other forms of infusion therapy and taurolidin or taurultam are added to maintain sterility, a wide range of other components are possible.

For therapy of metabolic acidosis, such other components will include buffer salts such as sodium acetate, sodium carbonate and/or hydrogen carbonate, sodium malate or trometamol. The polyol may, for example, be sorbitol.

For osmotherapy, for example, for treatment of cerebral oedema, the polyol is advantageously a combination of glycerol and glucose and an electrolyte such as sodium chloride and/or acetate may be present. Mannitol may also be used as polyol. Where an isotonic, isoionic electrolyte solution is required, the electrolyes may be such as to provide sodium, potassium, calcium, magnesium ions in their physiological proportions together with anions such as chloride, phosphate, glycerophosphate and/or acetate ions. The polyol may conveniently be glucose or fructose. Such solutions may alternatively be enriched in one or more cations, e.g. potassium and magnesium.

Where the solutions are intended for parenteral nutrition, e.g. peripheral venous nutrition, amino acids will be present as well as trace elements and vitamins. The amino acids will generally comprise L-isoleucine, L-leucine, L-lysine, L-methionine, L-phenylalanine, L-threonine, L-tryptphane, L-valine, L-arginine, L-histidine, L-alanine, L-glutamic acid L-proline and glycine. The proportions of the amino acids will generally be those conventional in parenteral nutrition. The vitamins which may be present may include pyridoxine (hydrochloride), inositol, riboflavin (5¹-phosphate sodium salt) and nicotinamide. Electrolytes where present may include sources of sodium, potassium, calcium and/or magnesium with acetate, malate or chloride ions.

Solutions for plasma replacement (e.g. in treatment of hypovolumic shock, burns, thrombosis etc) may include, for example, dextran or hydroxymethyl starch as plasma extender together with an electolyte such as sodium chloride and/or a further polyol such as glucose.

The following Examples are given by way of illustration only:

EXAMPLE 1

50.0 g Glucose were dissolved in 495 ml distilled water and the pH adjusted to 6.6 with N-sodium hydroxide. This solution was autoclaved and 10.0 g taurolidine were then added. After dissolution of the taurolidine, the volume was made up to 500 ml with sterile distilled water and sterile-filtered prior to sealing in a 500 ml flask.

EXAMPLE 2

100.0 g Glucose were dissolved in 495 ml distilled water and the pH adjusted to 6.6 with N-sodium hydroxide. This solution was autoclaved and 10.0 g taurolidine were then added. After dissolution of the taurolidine, the volume was made up to 500 ml with sterile distilled water and sterile-filtered prior to sealing in a 500 ml flask.

EXAMPLE 3

100.0 g Glucose were dissolved in 495 ml distilled water and the pH adjusted to 6.6 with N-sodium hydroxide. This solution was autoclaved and 20.0 g taurolidine were then added. After dissolution of the taurolidine, the volume was made up to 500 ml with sterile distilled water and sterile-filtered prior to sealing in a 500 ml flask.

EXAMPLE 4

Solution for therapy of metabolic acidosis

| 1000 ml infusion solution contains: | |
|---|---|
| Sodium acetate | 8.2 g |
| Sodium hydrogen carbonate | 4.2 g |
| Sodium L-malate | 6.2 g |
| Trometamol (THAM) | 4.0 g |
| Sorbitol | 50.0 g |
| Taurolidine | 30.0 g |
| in water for injection | |

EXAMPLE 5

Solution for osmotherapy

| 1 liter contains: | |
|---|---|
| Glycerol | 100.0 g |
| Glucose monohydrate for injection | 27.5 g |
| Sodium chloride | 25.0 g |
| Taurolidine | 30.0 g |

| 1 liter contains: | |
|---|---|
| in water for injection | |

EXAMPLE 6

Isotonic and isoionic electrolyte solution

| 1 liter contains: | |
|---|---|
| $Na^+$ | 3.151 g |
| $K^+$ | 0.156 g |
| $Ca^{++}$ | 0.066 g |
| $Mg^{++}$ | 0.030 g |
| $Cl^-$ | 3.900 g |
| Acetate | 2.173 g |
| Glucose Monohydrate for injection | 55.0 g |
| Taurolidine | 20.0 g |
| in water for injection | |

The taurolidine content may alternatively be 30.0 g The 20.0 g taurolidine may also be replaced by 30.0 g taurultam.

EXAMPLE 7

Isotonic and isoionic electrolytic solution

| 1 liter contains: | |
|---|---|
| $Na^+$ | 3.151 g |
| $K^+$ | 0.156 g |
| $Ca^+$ | 0.066 g |
| $Mg^{++}$ | 0.030 g |
| $Cl^-$ | 3.900 g |
| Acetate | 2.173 g |
| Fructose | 50.0 g |
| Fructose | 100.0 g |
| Taurolidine | 20.0 g |
| in water for injection | |

The taurolidine content may alternatively be 30.0 g The 20.0 g taurolidine may also be replaced by 30.0 g taurultam.

EXAMPLE 8

Isotonic and isoionic electrolytic solution with increased potassium content

| 1 liter contains | |
|---|---|
| $Na^+$ | 3.151 g |
| $K^+$ | 0.156 g |
| $Ca^{++}$ | 0.066 g |
| $Mg^{++}$ | 0.030 g |
| $Cl^-$ | 3.900 g |
| Acetate | 2.820 g |
| Fructose | 50.0 g |
| Taurolidine | 20.0 g |
| in water for injection | |

The taurolidine content may alternatively be 30.0 g The 20.0 g taurolidine may also be replaced by 30.0 g taurultam.

EXAMPLE 9

Electrolyte solution

| 1 liter contains: | |
|---|---|
| $Na^+$ | 1,129 g |

-continued

| 1 liter contains: | |
|---|---|
| K+ | 0.973 g |
| Mg++ | 0.061 g |
| Cl− | 1.741 g |
| H2PO4− | 0.960 g |
| Lactose | 1.781 g |
| Glucose Monohydrate for injection | 55.0 g |
| Taurolidine in water for injection | 20.0 g |

The taurolidine content may alternatively be 30.0 g.
The 20.0 g taurolidine may also be replaced by 30.0 g taurultam.
The potassium content may be varied between 0.05 and 24.9 millimol.

EXAMPLE 10

Isotonic sodium chloride solution containing hydroxyethyl-starch

| 1 liter contains | |
|---|---|
| 0-(2-Hydroxy-ethyl)-amylopectin hydrolysate (Hydroxyethyl starch) (Substitution grade 0.40–0.50) (Average molecular weight: 200,000) | 100.00 g or 60.00 g |
| Sodium chloride (Na+: 154 mmol, Cl−: 154 mmol) | 9.00 g |
| Glucose monohydrate for injection | 55.0 g |
| Taurolidine in water for injection | 20.0 g |

The taurolidine content may alternatively be 30.0 g
The 20.0 g taurolidine may also be replaced by 30.0 g taurultam.

EXAMPLE 11

Ringer solution

| 1 Liter contains: | |
|---|---|
| Na+ | 1.129 g |
| K+ | 0.052 g |
| Ca++ | 0.030 g |
| Cl− | 1.840 g |
| Glucose monohydrate for injection | 36.6 g |
| Taurolidine in water for injection | 20.0 g |

The taurolidine content may alternatively be 30.0 g
The 20.0 g taurolidine may also be replaced by 30.0 g taurultam.

EXAMPLE 12

Solution for osmotherapy

| 1 Liter contains: | |
|---|---|
| Na+ | 1.379 g |
| Cl− | 1.595 g |
| Acetate | 0.886 g |
| Ethoxy-azorutoside | 0.200 g |
| Sorbitol | 400.0 g |
| Taurolidine in water for injection | 20.0 g |

The taurolidine content may alternatively be 30.0 g
The 20.0 g taurolidine may also be replaced by 30.0 g taurultam.

EXAMPLE 13

Solution for osmotherapy

| 1 Liter contains: | |
|---|---|
| Mannitol | 200.0 g |
| Taurolidine in water for injection | 20.0 g |

The taurolidine content may alternatively be 30.0 g
The 20.0 g taurolidine may also be replaced by 30.0 g taurultam.

EXAMPLE 14

Solution with invert sugar

| 1 Liter contains: | |
|---|---|
| Sodium chloride | 2.483 g |
| Sodium acetate 3H2O | 3.742 g |
| Potassium chloride | 0.373 g |
| Calcium chloride | 0.153 g |
| Glucose Monohydrate for injection | 14.90 g |
| Fructose | 13.13 g |
| Taurolidine in water for injection | 20.0 g |

The taurolidine content may alternatively be 30.0 g
The 20.0 g taurolidine may also be replaced by 30.0 g taurultam.

EXAMPLE 15

Electrolyte solution with 10 mmol potassium

| 1 Liter contains: | |
|---|---|
| Sodium chloride | 4.968 g |
| Sodium acetate | 7.485 g |
| Potassium chloride | 0.746 g |
| Calcium chloride | 0.368 g |
| Magnesium chloride | 0.305 g |
| Taurolidine | 20.0 g |
| Glucose in water for injection | 55.0 g |

The taurolidine content may alternatively be 30.0 g
The 20.0 g taurolidine may also be replaced by 30.0 g taurultam.

EXAMPLE 16

Potassium-magnesium rich infusion solution

| 1 Liter contains: | |
|---|---|
| Xylitol | 70.0 g |
| Glucose Monohydrate for injection | 33.0 g |
| Malic acid | 2.5 g |
| Potassium chloride | 3.75 g |
| Magnesium chloride | 1.015 g |
| Magnesium acetate | 3.22 g |
| Tripotassium phosphate | 2.123 g |
| Taurolidine in water for injection | 20.0 g |

The taurolidine content may alternatively be 30.0 g
The 20.0 g taurolidine may also be replaced by 30.0 g taurultam.

EXAMPLE 17

Electrolyte solution

| 1 Liter contains | |
|---|---|
| Sodium chloride | 8.182 g |
| Potassium chloride | 0.373 g |
| Calcium chloride | 0.368 g |
| Magnesium chloride | 0.305 g |
| Fructose | 100.0 g |
| Taurolidine | 20.0 g |
| in water for injection | |

The taurolidine content may alternatively be 30.0 g
The 20.0 g taurolidine may also be replaced by 30.0 g taurultam.

EXAMPLE 18

Fully balanced L-amino acid solutions

| 1 Liter contains: Amino acid content | 5% | 10% |
|---|---|---|
| Amino acids | | |
| L-Isoleucine | 1.55 g | 3.10 g |
| L-leucine | 2.20 g | 4.40 g |
| L-Lysine monohydrochloride | 2.50 g | 5.00 g |
| L-Methionine | 2.10 g | 4.20 g |
| L-Phenylalanine | 2.20 | 4.40 g |
| L-Threonine | 1.00 g | 2.00 g |
| L-Tryptophane | 0.45 g | 0.90 g |
| L-Valine | 1.50 g | 3.00 g |
| L-Alanine | 6.00 g | 12.00 g |
| L-Arginine | 4.00 g | 8.00 g |
| L-Glutamic acid | 9.00 g | 18.00 g |
| Glycine | 10.00 g | 20.00 g |
| L-Histidine | 1.00 g | 2.00 g |
| L-Proline | 7.00 g | 14.00 g |
| Polyols: | | |
| Sorbitol | 50.00 g | 50.00 g |
| Xylitol | 50.00 g | 50.00 g |
| Ethanol | 50.00 g | — |
| Vitamins: | | |
| Ascorbic acid | 0.40 g | 0.40 g |
| Inositol | 0.50 g | 0.50 g |
| Nicotinamide | 0.06 g | 0.06 g |
| Pyrodoxine hydrochloride(B) | 0.04 g | 0.04 g |
| Riboflavin-5'-phosphate sodium | | |
| Electrolytes: | | |
| Potassium hydroxide | 1.68 g | 1.68 g |
| Magnesium acetate | 1.07 g | 1.07 g |
| Sodium hydroxide | 1.60 g | 1.60 g |
| L-Malic acid | 2.01 g | 0.67 g |
| Taurolidine | 20.00 g | 20.00 g |

The taurolidine content may alternatively be 30.0 g
The 20.0 g taurolidine may also be replaced by 30.0 g taurultam.

EXAMPLE 19

Complete solution for peripheralvenous nutrition

| 1 Liter contains: | |
|---|---|
| L-Isoleucine | 0.98 g |
| L-leucine | 2.33 g |
| L-Lysine monohydrochloride | 2.21 g |
| L-Methionine | 1.26 g |
| L-Phenylalanine | 1.16 g |
| L-Threonine | 1.26 g |
| L-Tryptophane | 0.49 g |
| L-Valine | 1.08 g |
| Arginine | 3.26 g |
| L-Histidine monohydrochloride | 1.09 g |
| Acetylcysteine | 0.26 g |
| Glycine | 3.64 g |
| L-Alanine | 6.06 g |
| L-(+)Glutamic acid | 2.01 g |
| L-Proline | 3.26 g |
| L-Serine | 3.26 g |
| N-Acetyl-L-tyrosine | 0.23 g |
| Sodium L-hydrogen glutamate H$_2$O | 3.98 g |
| Sodium chloride | 1.169 g |
| Potassium chloride | 2.237 g |
| Magnesium acetate 4 H$_2$O | 1.072 g |
| Calcium chloride 2 H$_2$O | 0.368 g |
| Glycerol-1(2)-dihydrogenphosphate mixed with its disodium salt (30/70% W/W)5 H$_2$O | 3.061 g |
| Sorbitol | 30.0 g |
| Xylitol | 30.0 g |
| Taurolidine | 20.0 g |
| in water for injection | |

The taurolidine content may alternatively be 30.0 g
The 20.0 g taurolidine may also be replaced by 30.0 g taurultam.

EXAMPLE 20

Electrolyte-free peripheral nutrition solution

| 1 Liter contains: | |
|---|---|
| L-Isoleucine | 7.52 g |
| L-leucine | 11.38 g |
| L-Lysine | |
| L-Methionine | 6.59 g |
| L-Phenylalanine | 7.76 g |
| L-Threonine | 6.78 g |
| L-Tryptophane | 2.91 g |
| L-Valine | 9.53 g |
| L-Histidine | 4.90 g |
| Sorbitol | 25.00 g |
| Xylitol | 25.00 g |
| Taurolidine | 20.00 g |
| in water for injection | |

The taurolidine content may alternatively be 30.0 g
The 20.0 g taurolidine may also be replaced by 30.0 g taurultam.

EXAMPLE 21

Dextran plasma replacement solutions

| 1 Liter contains: | | |
|---|---|---|
| (a) | Dextran(MW 40,000) | 100 g |
| | NaCl | 9 g |
| | Taurolidine | 20 g |
| | in water for injection | |
| (b) | Dextran(MW 40,000) | 100 g |
| | Glucose | 50 g |
| | Taurolidine | 20 g |
| | in water for injection | |
| (c) | Dextran (MW 40,000) | 60 g |
| | NaCl | 9 g |
| | Taurolidine | 20 g |
| | in water for injection | |
| (d) | Dextran(MW 70,000) | 60 g |
| | Glucose | 50 g |
| | Taurolidine | 20 g |
| | in water for injection | |
| (e) | Dextran(MW 70,000) | 30 g |
| | Taurolidine | 20 g |
| | in Ringer-lactate | |
| | (Na$^+$ | 130 m/mol |
| | K$^+$ | 5.4 m/mol |
| | Ca$^{++}$ | 0.9 m/mol |
| | Mg$^{++}$ | 1.0 m/mol |

-continued

| 1 Liter contains: | |
|---|---|
| Cl⁻ | 27 m/mol) |

The taurolidine content may alternatively be 30.0 g

The 20.0 g taurolidine may also be replaced by 30.0 taurultam.

I claim:

1. A liquid pharmaceutical composition for parenteral infusion or injection into a patient comprising a liquid aqueous solution containing a bactericide selected from the group consisting of 1-5 weight % of taurolidine and 1-7.5 weight % of taurultam, together with 3-40 weight % of a parenterally acceptable polyol.

2. A pharmaceutical composition as claimed in claim 1 wherein the polyol is glycerol, a sugar or a sugar alcohol.

3. A pharmaceutical composition as claimed in claim 2 wherein the sugar alcohol is sorbitol or xylitol.

4. A pharmaceutical composition as claimed in claim 1 wherein the polyol is glucose.

5. A pharmaceutical composition as claimed in claim 4 comprising taurolidine at a concentration in the range 3 to 4% by weight and glucose at a concentration in the range 15 to 25% by weight.

6. A pharmaceutical composition as claimed in claim 1 wherein the polyol is fructose.

7. A pharmaceutical composition as claimed in claim 1 wherein the concentration of taurolidine is in the range 2 to 3% by weight or the concentration of taurultam is in the range of 3 to 5% by weight.

8. A pharmaceutical composition as claimed in claim 1 further comprising an additive selected from the group consisting of an electrolyte, one or more amino acids, trace elements and vitamins.

9. A pharmaceutical composition as claimed in claim 1 wherein the concentration of taurolidine is in the range of 2 to 3% by weight.

10. A pharmaceutical composition as claimed in claim 1 wherein the concentration of taurultam is in the range 3 to 5% by weight.

* * * * *